United States Patent [19]

Pyers

[11] 4,244,358

[45] Jan. 13, 1981

[54] ROLLOVER BED HAVING PALLET WITH FLEX POINTS AND CONSTANT TRACTION MAINTAINING APPARATUS

[76] Inventor: Noel Pyers, 4242 E. Ware Rd., Tucson, Ariz. 85711

[21] Appl. No.: 74,131

[22] Filed: Sep. 10, 1979

[51] Int. Cl.[3] .......... A61F 5/00

[52] U.S. Cl. .......... 128/74; 128/75; 128/84 R; 5/61

[58] Field of Search .......... 128/75, 68, 71, 72, 128/73, 74, 75, 84 R; 5/61

[56] References Cited

U.S. PATENT DOCUMENTS

| | | | |
|---|---|---|---|
| 2,690,177 | 9/1954 | Hogan | 128/84R |
| 3,568,669 | 3/1971 | Stites | 128/71 |
| 3,766,912 | 10/1973 | Daniels | 128/71 |
| 3,821,953 | 7/1974 | Mikan | 128/71 |
| 4,157,089 | 6/1979 | Loughrey | 128/74 |

*Primary Examiner*—John D. Yasko

*Attorney, Agent, or Firm*—Cahill, Sutton & Thomas

[57] ABSTRACT

A rollover bed having a pallet with a pair of central hinge points to allow mid-body flexing and knee joint flexing of a patient supported by the pallet is capable of maintaining constant angular traction on the patient while the pallet is flexed to angles which are comfortable to the patient. The bed also maintains the constant angular traction on the patient during the operation of turning the patient over.

14 Claims, 9 Drawing Figures

ROLLOVER BED HAVING PALLET WITH FLEX POINTS AND CONSTANT TRACTION MAINTAINING APPARATUS

BACKGROUND OF THE INVENTION

1. Field of the Invention

The invention relates to hospital beds and beds for supporting incapacitated or partially incapacitated patients, and more particularly to beds of the type capable of maintaining traction on a patient supported thereby.

2. Description of the Prior Art

It is sometimes necessary that persons who are injured or handicapped, either temporarily or permanently, must be maintained in traction for certain periods of time in the course of treatment and thereapy for their conditions or injuries. For example, patients with various types of neck or back injuries may need to have their necks or legs maintained in traction for relatively long periods of time to allow healing of the injury. In other cases, a patient's condition or injury may require that his head or certain limbs be maintained in traction at a particular angle to alleviate pain.

Several prior hospital beds, including those disclosed in U.S. Pat. Nos. 2,690,177 and 3,302,218, are capable of maintaining constant traction on a patient lying in the bed when the patient is rotated or "turned over". It is very important to be able to turn over patients confined to a hospital bed so that they are shifted from a position wherein they are lying on their back to a position wherein they are lying on their stomach in order to avoid serious discomfort which results when a patient lies only in one position for a long period of time. If the patient is required to be maintained in traction, it may be very desirable that the traction be maintained while the patient is being turned over to avoid pain or injury to the patient. The beds disclosed in the above mentioned patents accomplish this goal under certain conditions. However, sometimes it is necessary that traction be applied to the head or a limb of a patient in a direction which is substantialy different that the direction of the axis about which the bed rotates. The beds shown in the above mentioned patents are incapable of maintaining constant traction on a patient at a substantial angle measured with respect to the turning axis of their patient supporting frames or pallets.

Accordingly, it is an object of the invention to provide a rollover bed which is capable of maintaining constant traction at a substantial angle measured with respect to the turning axis of the bed while the patient is being turned.

In many cases, it is highly desirable that a rollover bed to which an incapacitated patient is confined be flexible at its midpoint so that the body of the patient can flex so as to allow him to sit at an at least upright angle so that his upper body is not in a completely prone position. Both the physical comfort and the psychological welfare of the patient may be greatly benefited by allowing the patient to sit in an at least partially upright position. It is especially important to the mental welfare of persons confined to a bed for a long time that they not always have a look upward from a completely prone position to all who visit or attend to them. The beds shown in the above mentioned patents are not capable of midpoint flexing or knee joint flexing, nor is any other known bed capable of simultaneous midpoint or knee flexing and maintaining constant traction tension on a patient.

Accordingly, it is another object of the invention to provide a bed which is capable of allowing midbody and/or knee joint flexing of a patient supported thereon while maintaining constant traction tension on the patient during the flexing operation and while the patient remains in the flexed position.

It is yet another object of the invention to provide a rollover bed capable of providing midbody flexing for a patient thereon.

It is yet another object of the invention to provide a rollover bed capable of providing midbody flexing of a patient thereon and also capable of maintaining constant angular tension of the patient during both rollover and midbody flexing operations.

A novelty search directed to the present invention uncovered the following additional U.S. Pat. Nos., which are believed to be illustrative of the state of the art pertaining to the invention: 4,127,906; 3,862,454; 3,238,539; 3,266,061; 3,530,514; 3,581,320 and 3,827,089.

SUMMARY OF THE INVENTION

Briefly described, and in accordance with one embodiment thereof, the invention provides an apparatus for supporting a patient and flexing the body of the patient while maintaining a constant tension at a constant angle on a part of the patient's body. The apparatus also is capable of turning the patient over while maintaining constant traction tension at a constant angle on a part of patient's body. In the described embodiment of the invention, an undercarriage having a plurality of castors thereon includes first and second end posts. A pallet has first and second frame sections hingeably connected together at a central portion of the pallet so that the body of the patient lying on the pallet can be flexed. The respective ends of the frame sections of the pallet are rotatably supported by the end posts. The first end of the pallet is supported by means of a rollover hoop assembly rotatably supported at the top of the first end post. The first end of the pallet rests on a cross bar of the rollover hoop assembly. The second end of the pallet is supported by a pivot assembly which is rigidly attached to the end of the second frame section of the pallet. The pivot assembly includes a T-shaped element having a verticle member and a tubular horizontal member. The lower end of the verticle member is pivotally attached to the upper end of second end post. A tubular trunnion has a first end rigidly attached to the end of second frame section of the pallet. The trunnion is rotatably supported in the tubular horizontal member of the T-shaped element. A traction cord support assembly is adjustably connected to the trunnion. The traction cord support assembly includes an outrigger rod which extends outwardly at an acute angle the axis of the trunnion. The axis of the trunion is substantially parallel to the plane of the second frame section of the pallet. The outrigger rod supports a plurality of support pulleys which in turn support the traction cord. The traction cord extends through the center of the hollow trunion and passes over an end pulley supported on the second end of the trunion and has a first end connected to a weight which maintains constant tension in the traction cord. The opposite end of the traction cord extends from the end pulley and is connected to the head or a limb of the person lying on the pallet.

The hinged section of the pallet is supported by a hydraulic lift system which includes an L-shaped member having one end hingeably connected to the second end post. A hydraulic cylinder having a first end pivotally anchored to the undercarriage and also having a moveable rod pivotally connected to the L-shaped member causes the L-shaped member to rotate about its pivotally anchored end, raising or lowering the second end of the L-shaped member. A cross bar is attached to the second end of the L-shaped member, causing it to support the center of the pallet, thereby controlling the degree of flexing of the pallet about the hinged section thereof, thereby also controlling the degree of midbody flexing of the patient supported by the pallet.

As the center of the pallet is raised or lowered, the trunnion maintains a fixed relationship to the second frame section, and consequently the outrigger rod also maintains a fixed relationship to the second frame section of the pallet. Consequently, the traction cord extending from an end, one of the support pulleys also maintains a constant relationship to the portion of the patient's body to which traction is being applied. Thus, the angle of traction applied to the patient's body is maintained constant during flexing of the patient's body, and the tension in this traction cord is maintained constant by the weight attached to the first end of the cord.

An auxiliary pallet may be placed over the patient and bound to the first pallet by means of tape, sandwiching the patient between the two pallets. One end of the auxiliary pallet is placed between the main pallet and a second support bar of the rollover hoop. A second end of the auxiliary pallet includes two separable frame members which can be separated to allow the separable frame members to be passed around the traction cord, re-connected together, and rigidly attached to the pivot assembly. The main and auxiliary pallets then can be rotated to turn the patient over. The trunnion and outrigger bar rotate at the same rate as the pallets as the patient is turned over by 180 degrees. Thus, the relationship of the end cord support pulley to the portion of the patient's body being held in traction is maintained constant during the rollover operation.

In another embodiment of the invention, an additional flex points is provided in the pallet, enabling flexing of the patient's knees. A second hydraulic cylinder assembly is provided to control the amount of flexing of the patient's knees.

In another embodiment of the invention, one or both end posts include hydraulic jacks which enable either end of the patient to be raised or lowered to a suitable level.

DESCRIPTION OF THE INVENTION

Figure 1:
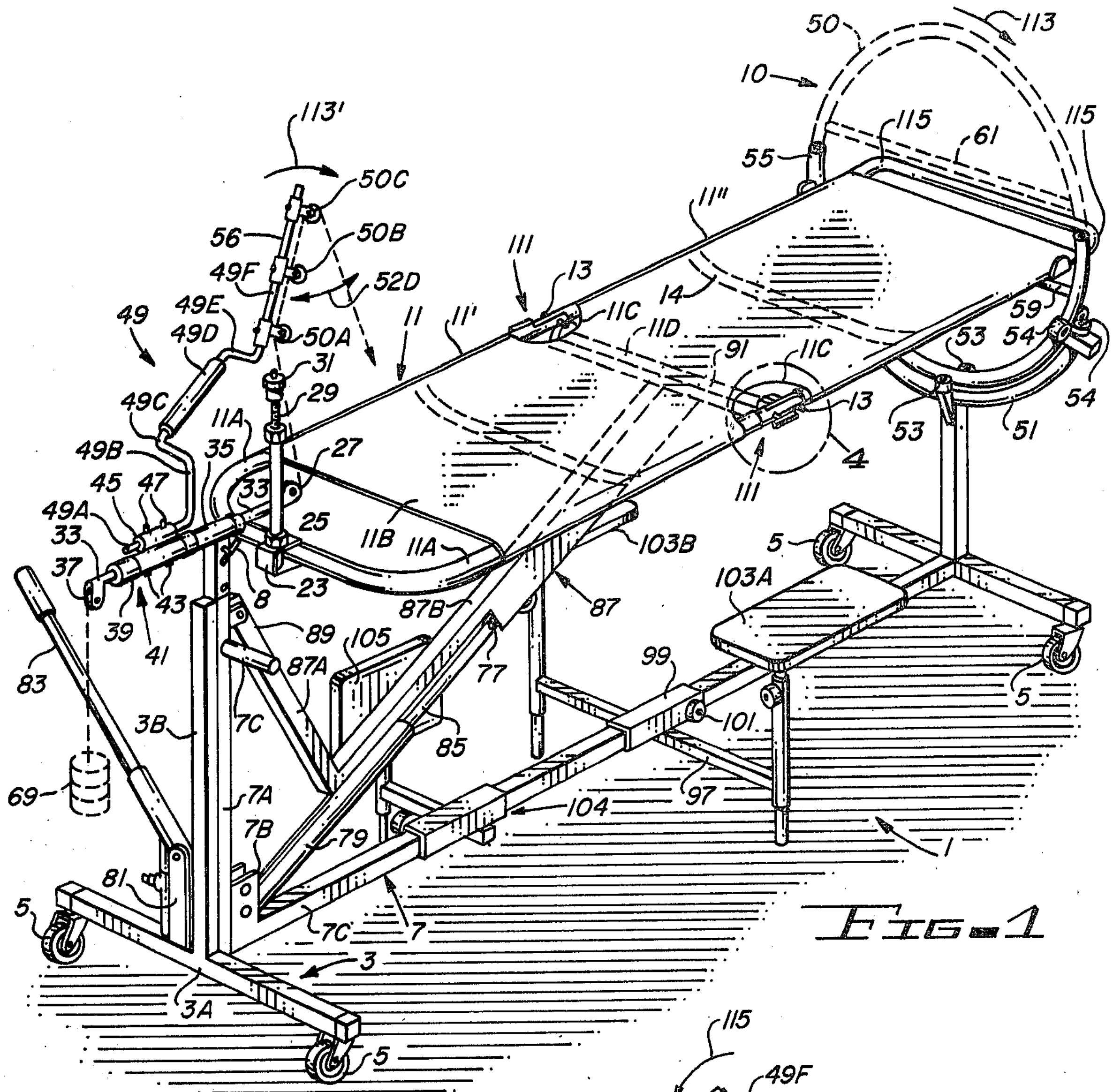
FIG. 1 is a perspective view of the bed assembly of the present invention.

Referring now to FIG. 1, rollover bed 1 includes left and right T-shaped frame supports 3 and 9 which are connected together by a transverse member 7. T-shaped end support 3 includes a horizontal member 3 and an upright support post 7A attached thereto. End support 9 includes horizontal member 9B and vertical member 9A. Horizontal member 3A and 9B are supported by means of a plurality of castors 5, as indicated in FIG. 1.

Upright post 9A supports a semicircular member 51. A plurality of side rollers 53 and 54 are attached to semicircular member 51. As shown in further detail in FIG. 6, a pair of bottom rollers 56 disposed in respective slots in semicircular member 51 support a rollover hoop 10.

Figure 6:
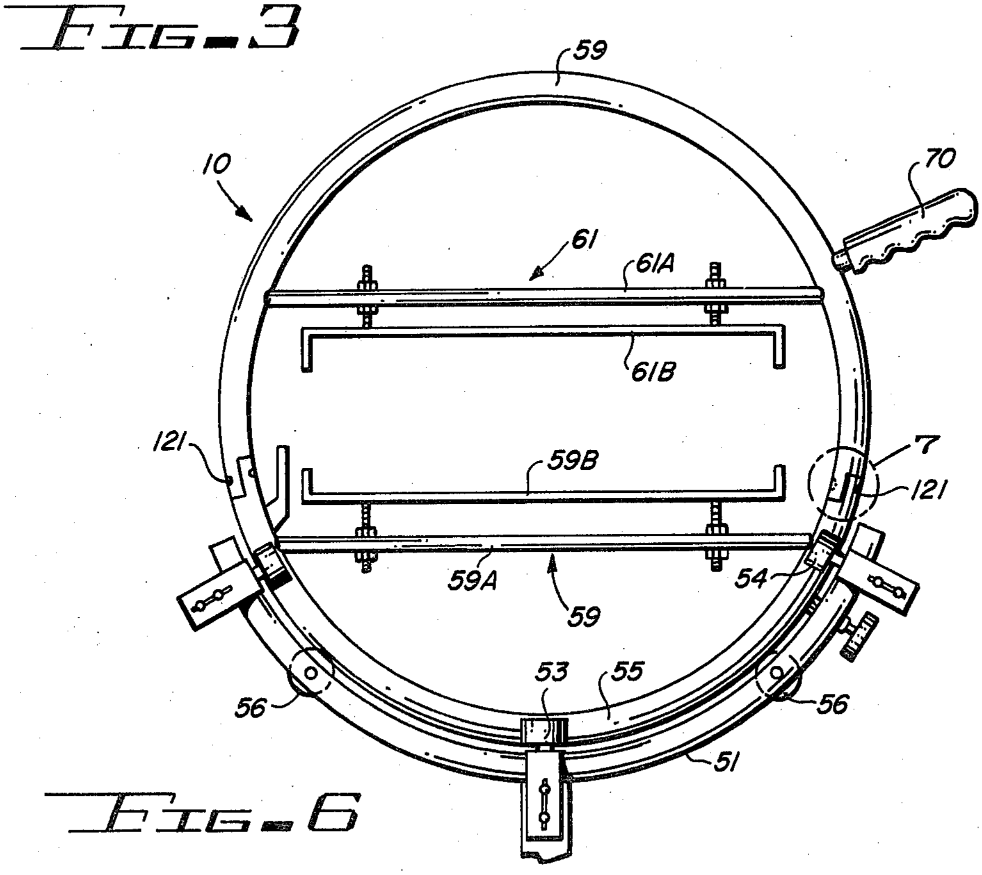
FIG. 6 is a partial end view illustrating the turnover hoop of the bed assembly of FIG. 1.
Figure 7:
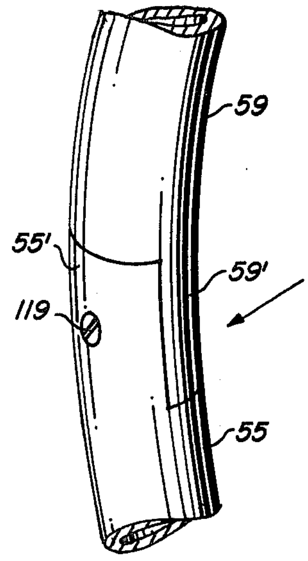
FIG. 7 is a partial perspective view of the connected sections of the rollover hoop.

As indicated by the dotted lines in FIG. 7, the upper section 57 of rollover hoop 10 is removable. A patient support frame or pallet 11 is supported at its right end by means of pallet support member 59, shown in detail in FIG. 6. Pallet support member 59 is rigidly attached to the lower section 55 of rollover hoop 10.

Pallet 11 includes a tubular frame 11A having tubular side members rigidly braced apart by a pair of separator bars 12 and 14, as shown in FIG. 1. Canvas 11B is tautly stretched across the tubular side portions 11A and 11E (see FIG. 4) of pallet 11, providing a support surface for supporting a patient. Spacer bars 12 and 14 prevent the tubular side portions 11A and 11B of pallet 11 from being pulled together by the weight of the patient on canvas 11B.

The left hand end (in FIG. L) of pallet 11 is attached by means of bracket 23, rod 25, and trunnion 33 to outrigger assembly 49, which is pivotally attached to left upright post 7A.

L-shaped support 35, 35A is pivotally connected by means of pin 58 (FIG. 2) to upright 7A. L-shaped member 35A, 35 includes a support arm 35A and a tubular bearing section 35. Trunnion 33 extends through bearing support 35. Trunnion 33 is perpendicular to and connected to pallet support member 25, which is rigidly connected to bracket 23. Outrigger assembly 49 is adjustably connected to trunnion 33.

Pallet 11 includes a first section 11' and a second section 11''. First and second sections 11' and 11'' are hingeably connected together at hinge joints 111 (see FIGS. 1, 4, and 5.)

Figure 4:
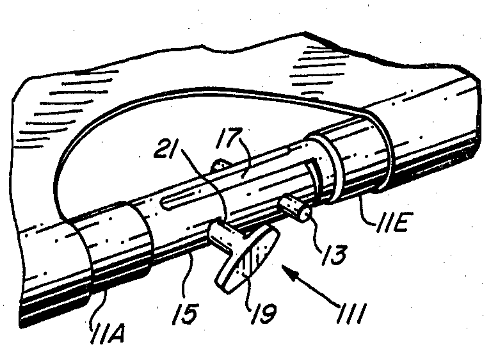
FIG. 4 is a partial expanded perspective view of one flex joint of the pallet of the bed assembly shown in FIG. 1.
Figure 5:
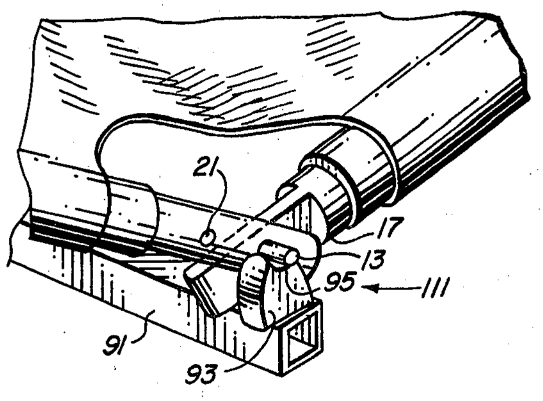
FIG. 5 is a partial perspective view illustrating the flexing joint of FIG. 4 in its flexed configuration.

Referring now particularly to FIGS. 4 and 5, the details of hinge joints 111 of pallet 11 are shown. Tubular frame member 11A has a bifurcated end section 15. Tubular frame member 11E has a prong shaped end 17 which fits between the tines of bifurcated end 15. Prong 17 and bifurcated end 15 are hingeably connected together by means of a pivot pin 13.

If it is desired that pallet section 11' and 11'' be rigidly connected together such that no flexing occurs at hinge joints 111, a removable pin 19 is inserted through holes spaced from pin 13 and extending through the tines of bifurcated end 15 and pring 17, as shown in FIG. 4.

However, if it is desired that pallet 11 flex at hinge joints 111 in order to make the patients supported by pallet 11 more comfortable, pins 19 may be removed from holes 21 (FIG. 5).

Referring now to FIG. 1, a support bar 91 attached to a hydraulicly controlled support beam 87 has a pair of pin-receiving elements 93 attached thereto. Each of pin-receiving elements 93 has a V-shaped groove 95 in which one of pins 13 rests, as shown in FIG. 5.

Referring again to FIG. 1, support beam 87 includes a first beam section 87B, which is attached at a right angle to a second beam section 87A. The extreme end of beam section 87A is pivotally attached by means of pivot pin 89 to first upright 7A. A hydraulic cylinder 79 having a moveable rod 85 is attached to an intermediate point 77 of beam section 87B by means of a pivot pin. The body of cylinder 79 is pivotally attached by means of pivot pin 7B to member 7. A hydraulic pump 81 actuated by handle 83 can be operated in conjunction with a release valve (not shown) to gradually raise or lower beam 87 and crossmember 91, thereby raising and lowering hinge joints 111 of pallet 11 and thereby controlling the amount of midbody flexing of a patient supported on pallet 11. A reservoir for hydraulic fluid utilized in pump 81 is contained in hollow upright member 3B, to which upright post 7A is connected to provide structural strength.

Figure 8:
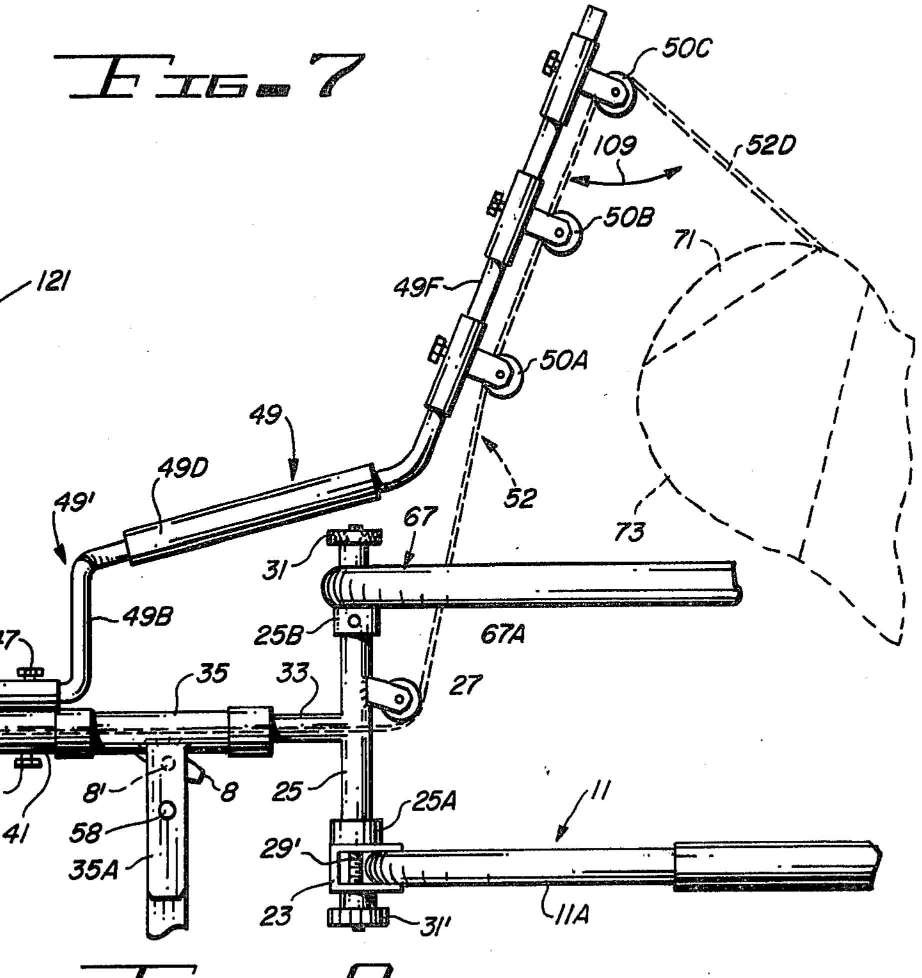
FIG. 8 is a partial perspective view illustrating the outrigger and trunnion of FIG. 1, its connection to a support post, and auxiliary pallet used to aid in turning over of a patient supported by the bed assembly of FIG. 1.

The details of pivotable outrigger assembly 49 are not set forth in detail with particular reference to FIGS. 1 and 8.

As previously explained, trunnion 33 extends through tubular bearing section 35. Trunnion 33 can freely rotate in bearing section 35 as pallet 11 rotates. Rollover hoop 10 rotates freely by virtue of side rollers 53 and 54 and bottom rollers 56, previously described. Thus, pallet 11 can be easily rotated about its longitudinal axis.

Collar 41 is rigidly attached, as by welding to collar 45. Trunnion 33 extends through collar 41, and is secured at a predetermined angle with respect to the plane of pallet 11 by means of set screws 43. An outrigger bar 49 (FIG. 8) includes sections 49A, 49B, 49C, 49E, and 49F. Section 49C extends through collar 45, and is rigidly secured thereto at a predetermined angle by means of set screws 47. Section 49B is approximately perpendicular to section 49A, and section 49C is approximately perpendicular to the plane defined by sections 49A and 49B. Section 49E is parallel to section 49C.

Section 49D forms an angle of roughly 30 degrees with respect to section 49A. Section 49F is approximately perpendicular to section 49E, and supports three traction cord support pulleys 50A, 50B, and 50C.

A pulley 27 is supported by rod 25, and end pulley 37 is supported at the extreme outward end of trunnion 33.

Figure 2:
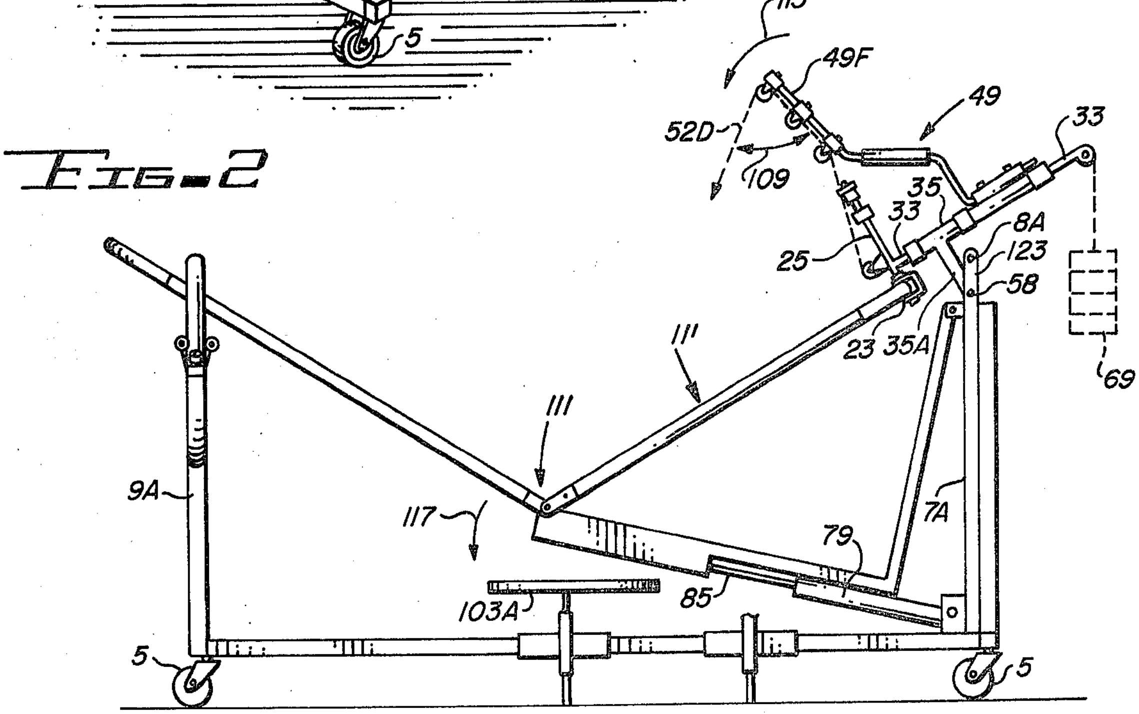
FIG. 2 is a partial side view of the device of FIG. 1.

Trunnion 33 is tubular, so that a traction cord 52 having a traction weight 69 extends over end pulley 37, and through the center of trunnion 33, around pulley 27, and along pulleys 50A, 50B, and 50C, as shown in FIGS. 1, 2 and 8.

In accordance with the present invention, section 52D of traction cord 52 is attached to the head or a limb of a patient supported by pallet 11 to maintain traction on the patient as a substantial predetermined angle from the axis of rotation of pallet 11. By way of example, section 52D of traction cord 52 can be attached to a head support 73 of the head 71 of a patient, as shown in FIG. 8.

For purposes of discussion herein, it will be assumed that it is desired to maintain constant traction on the patient at an angle indicated by arrow 109 in FIGS. 1, 2 and 8, during the procedures of turning the patient over and adjusting the level of hinge joints 111 in order to flex the body of the patient.

In operation, it now can be seen that if rollover hoop 10 is rotated in the direction indicated by arrow 113 (FIG. 1), outrigger assembly 49 also rotates in the direction by the same number of degrees, as indicated by arrow 113'. End pulley 37 is supported by a bracket which rotates on the end of trunnion 33, so that traction weight 69 maintains and pulley 37 in the configuration shown in FIG. 1 as rollover bar 10, pallet 11, and outrigger assembly 49 all rotate together. Thus, it easily can be seen that constant traction is maintained on traction cord segment 52D during turning the patient over. (The manner in which a second pallet 67 (FIG. 8) is utilized in conjunction with section 57 of rollover hoop 11 will be described subsequently.)

Next, it readily can be seen that if pressure is released in the hydraulic cylinder 79, the end of support beam 87 is lowered in the direction indicated by arrow 117 in FIG. 2, causing hinge joint 111 to lower accordingly. Since outrigger assembly 49 is rigidly connected to the end of frame 11A of pallet section 11' by means of trunnion 33 and support rod 25, outrigger assembly 49 rotates at exactly the same rate as pallet section 11', as indicated by arrow 115. Consequently, the patient (not shown) will have his midsection flexed. The portion of the patient's body supported by pallet section 11' will maintain a constant relationship to outrigger assembly 49, and consequently angle 109, the angle which traction cord section 52D makes with section 49F of outrigger assembly 49, remains constant. Thus, constant angular traction on the patient is maintained during midsection flexing as well as during rollover of the patient.

Figure 3:
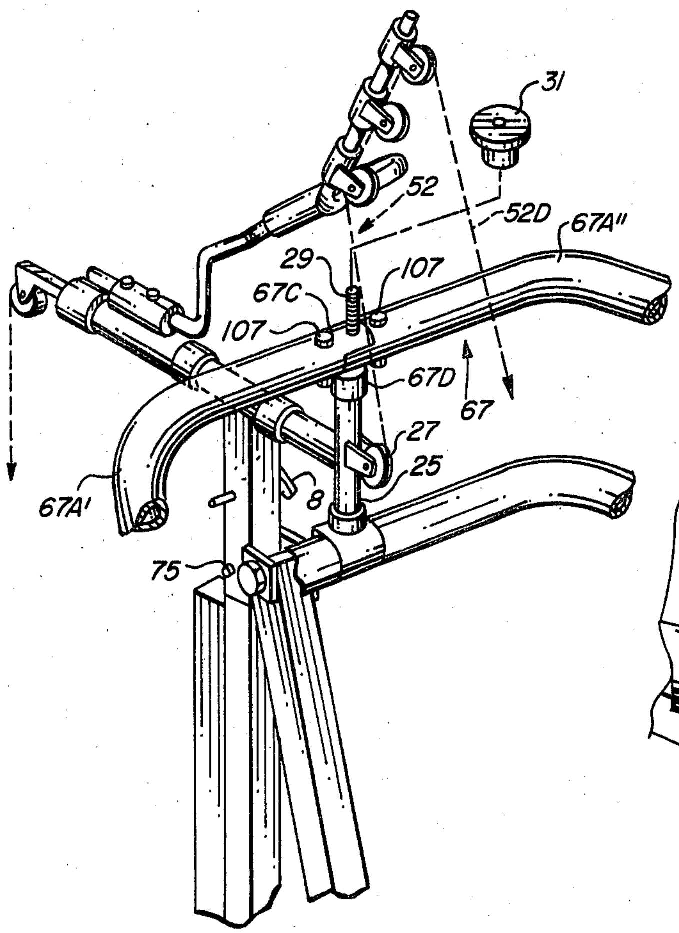
FIG. 3 is a partial enlarged perspective drawing illustrating one end post and the traction-maintaining outrigger and trunnion assembly of the device of FIG. 1.

As previously mentioned, rollover of a patient is accomplished by using a second or auxiliary pallet, indicated by reference numeral 67 in FIG. 8. Pallet 67 can be similar in construction to pallet 11, except that the end attached to support rod 25 assembly 49 is "split", as shown in FIG. 3. Referring to FIG. 3, frame 67A of auxiliary pallet 67 includes two sections 67A' and 67A''. Section 67A' has an extension 67C which mates with a similar extension 67D extending from frame section 67A''. The two mating sections can be rigidly attached together by means of bolt and nut 107. Bolt 29 extends upward from rod 25 and through aligned holes in sections 67C and 67D. Frame 67A is secured to rod 25 by means of nut 31.

The manner of using auxiliary pallet 67 is to place it over the patient supported by pallet 11, attaching frame 67A to rod 25 in the manner described above. The rear ends of auxiliary pallet and main pallet 11 extend between pallet supports 59B and 61B which are attached to rollover hoop 10, as shown in FIG. 6. VELCRO tape is wound around the two frames, sandwiching the patient between them. The reason that frame 67A of auxiliary pallet 67 is split into section 67A' and 67A'' is to allow sections 67C and 67D to be passed around traction cord section 52D without disturbing the traction applied to the patient.

Once auxiliary pallet 67 has been secured to the patient and main pallet 11 in the manner described above, a nurse or attendant can grasp handle 70 of rollover hoop 6 (FIG. 6) and rotate the assembly counterclockwise about the longitudinal axis of pallet 11 by 180 degrees, so that auxiliary pallet 67 supports the patient and main pallet 11 rests on top of the patient. Thus, the patient has been turned over, with the traction being maintained constant. It will now be appreciated that the configuration of sections 49C, 49D, and 49E shown in FIG. 1 is necessary to allow rotation of outrigger assembly 49 by a full 180 degrees. Otherwise, upright 7A would prevent a full 180 degrees of rotation.

Next, the VELCRO wrapping is removed, and pallet 11 (which is now above the patient) is removed by loosening nut 31′, slipping bracket 23 over bolt 29′, and withdrawing the rear end of pallet 11 from rollover hoop 10.

Section 59 of rollover hoop 10 is connected to section 55 thereof by means of two joints 121. The manner of connecting accomplished by junctions 121 is illustrated in FIG. 7, wherein it is seen that section 59 includes an extension 59′ having a semicircular cross section. Section 55 has an extension 55′ which also has a semicircular cross section and mates with section 59′. A bolt and screw 119 extend through sections 55′ and 59′ to securely engage section 59 to section 55.

Comfort of a patient awarded by pallet 11 is further increased by means of adjustable arm rests 103A and 103B, which are both supported by cross bar 97. Cross bar 97 is attached to a sliding bracket 99 which can be adjustably positioned along number 7C. Similarly, a sidetable 105, which can be lowered or raised and longitudinally adjusted, can be utilized for holding a basin or other objects near the patient's head.

Handle 7C, attached to upright 7A assists a person taking care of the patient in rolling bed 1 along a floor.

Figure 9:
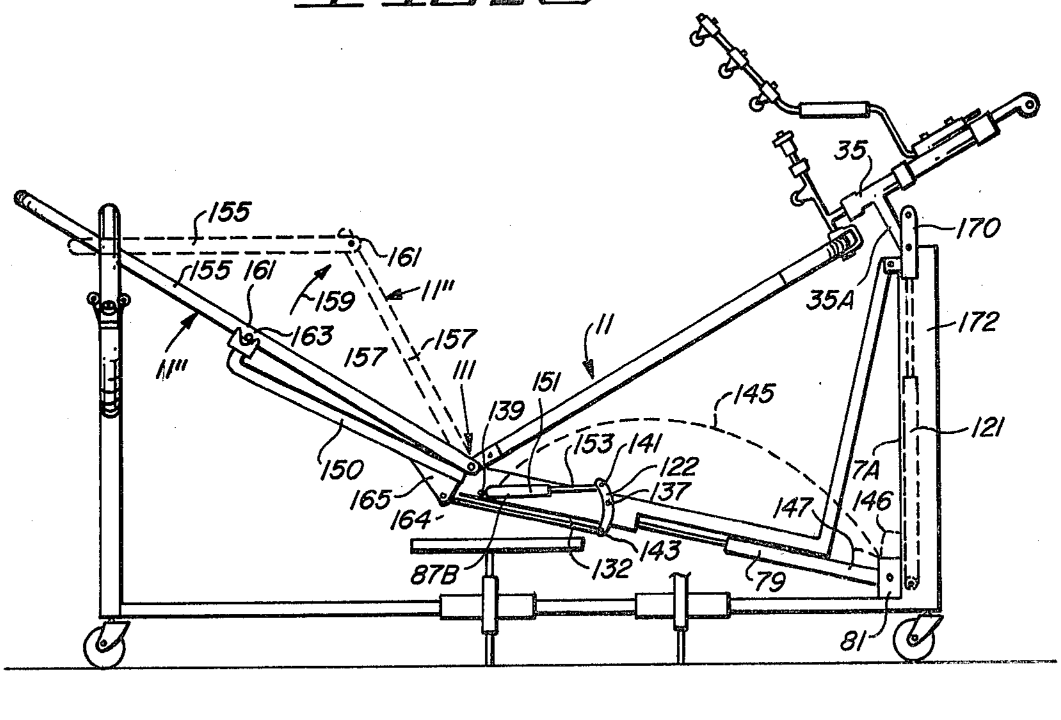
FIG. 9 is a side view of an alternate embodiment of the invention.

An alternate embodiment of the rollover bed of FIGS. 1–8 is shown in FIG. 9, wherein pallet 11 further includes knee hinge joints 161, which are similar in configuration to the joints shown in detail in FIGS. 4 and 5. Pallet section 11′ includes two subsections 155 and 157 hingedably connected together by knee joints 161. Subsections 155 and 157 can be hinged with respect to each other by raising knee joints 161 in the direction indicated by arrow 159, producing the configuration of pallet section 11′ indicated by the dotted lines in FIG. 9.

The varient embodiment of the invention shown in FIG. 9 includes a second hydraulic cylinder 151 pivotally connected at one end to a fixed point of beam member 87B by means of pin 139. Hydraulic cylinder 151 includes a moveable rod 153 which is pivotally connected to a first end of crank member 122. Crank member 122 is pivotally connected by means of pin 137 to another fixed point of beam member 87B. The opposite end of crank member 122 is connected by means of pin 143 to one end of transfer rod 132. The other end of transfer rod 132 is connected to beam 150 which is pivotally connected at one end to joint 111, previously described. The opposite end of beam 150 supports a cross bar similar to cross bar 91, shown in FIG. 1. That cross bar carries a pair of grooved joint supports similar to those indicated by reference numeral 93 in FIG. 5.

An extension 165 extends downward from beam 150. A pivot pin 164 connects transfer rod 132 to the lower end of lever arm 165.

In operation, when moveable rod 153 is forced outward from hydraulic cylinder 151, crank member 122 rotates clockwise, forcing transfer rod 132 toward lever arm 165, causing beam 150 to rotate in the direction indicated by arrow 159. This raises knee joint 161, lifting section 11′ of pallet 11 to the position indicated by the dotted lines in FIG. 9.

The elevation of the right end of pallet 11, as shown in FIG. 9, can be raised or lowered in the embodiment of the invention shown in FIG. 9 by means of a third hydraulic cylinder 121 contained within hollow upright 7A. Upright 7A serves as a sleeve for a vertically slideable pivot support 170, to which T-shaped member 35, 35A is pivotally attached. A moveable rod 172 extends from hydraulic cylinder 121 and is attached to the bottom of pivot support 170.

A plurality of pneumatic tubes, indicated by dotted lines 145, 146, and 147 are coupled by means of hydraulic valves, joints 111 and 161 of pallet 11 can be selectively lowered or raised, and the extreme right-hand end of pallet 11 can also be lowered or raised; these operations can all be performed by actuating pump handle 83 (FIG. 1). During all of these operations, constant traction is maintained on a patient supported by pallet 11.

While the invention has been described with reference to several embodiments thereof, those skilled in the art can readily provide variations in the disclosed structure without departing from the true spirit and scope of the invention, which is intended to be limited only as indicated in the following Claims.

All the invention has been described with reference to several embodiments thereof, those skilled in the art can readily provide obvious variations to the disclosed structure without departing from the true spirit and scope of the invention.

I claim:

1. An apparatus for supporting a patient and maintaining constant traction on the patient, said apparatus comprising in combination:

(a) an undercarriage having first and second ends;

(b) first and second end members attached to the first and second ends of said undercarriage;

(c) first pallet means for supporting a patient, said first pallet means having first and second ends thereof and also including first and second sections, said first and second sections being hingeably connected;

(d) first hinge means for hingeably connecting said first and second sections;

(e) first pallet support means connected to said first end member for supporting the first end of said first pallet means;

(f) second pallet support means connected to said second end member for supporting the second end of said first pallet means;

(g) first adjustable support means for adjustably supporting and controlling the height of the hinged portions of said first pallet means;

(h) traction means for maintaining constant tension at a constant angle on a portion of the patient's body, said traction means including i. a traction cord being first end and also having a second end for connection to a part of the patient's body, ii. means connected to the second end of said traction cord for maintaining a constant tension in said traction cord, iii. cord support means rigidly connected to said first end support means, said cord support means maintaining a portion of said traction cord in fixed relationship to said second section of said first pallet means during pivotry of said first and second sections of said first pallet means about said first hinged means, whereby the body of the patient can be flexed by raising and lowering the hinged portion of said flexed first patient support means by means of said first adjustable support means without significantly altering either the traction tension or angle of application thereof to the patient.

2. The apparatus of claim 1 wherein said first pallet means is pivotally supported by said first and second pallet support means to permit rotation of said first pallet about a longitudinal axis of said pallet means.

3. The apparatus of claim 2 wherein first pallet support means includes a rollover hoop assembly having a first cross bar for supporting a first end of first pallet means.

4. The apparatus of claim 3 wherein said second pallet support means includes a pivotal connecting means rigidly attached to the second end of said first pallet means and pivotally connected to said second end member.

5. The apparatus of claim 4 wherein said cord supporting means is rigidly connected to said pivotal connecting means.

6. The apparatus of claim 5 wherein said pivotal connecting means includes a trunnion rigidly connected to the second end of said first pallet means, said trunnion being tubular.

7. The apparatus of claim 6 wherein said trunnion is parallel to the plane of the second section of said first pallet means, and wherein said pivotal connecting means includes a bearing means through which said trunnion extends, said trunnion rotating in said bearing means as said first pallet means rotates.

8. The apparatus of claim 7 wherein said cord supporting means includes a first pulley over which said traction cord passes and from which said traction cord extends to a part of the patient's body to which traction is applied, said cord supporting means further including a pulley support member rigidly attached to said trunnion, said first pulley being supported a predetermined distance from a longitudinal axis of said trunnion, whereby traction is maintained on the patient at a predetermined angle with respect to the plane of the second section of said first pallet means.

9. The apparatus of claim 8 wherein said traction cord extends from said first pulley to a second pulley rigidly connected to said trunnion through a hole through said trunnion, over a third pulley pivotally supported by said trunnion to a traction weight, whereby a substantially constant traction tension force is maintained in said traction cord.

10. The apparatus of claim 5 wherein said first adjustable support means includes a first hydraulic cylinder attached to said undercarriage and a hydraulic pump system for actuating said first hydraulic cylinder, said first hydraulic cylinder having a moveable rod, said first adjustable support means further including means connected to said moveable cylinder for engaging a point of said first pallet means disposed between said first and second ends of said first pallet means to effect raising and lowering the midportion of said first pallet means, causing pivoting of said first and second sections of said first pallet means about said first hinge means in response to operation of said hydraulic pump system.

11. The apparatus of claim 10 further including second hinge means, said first section of said first pallet means further including first and second subsections pivotally connected together by said second hinge means.

12. The apparatus of claim 11 further including second adjustable support means for adjustably supporting and controlling the height of a portion of said first pallet means adjacent second hinge means.

13. The apparatus of claim 5 further including means for adjusting the height of said pivotal connecting means, whereby the second end of said first pallet means can be controllably raised or lowered.

14. The apparatus of claim 9 wherein said pivotal connecting means further includes means for rigid attachment to an auxiliary pallet means, and wherein said rollover hoop includes a second cross bar for supporting the opposite end of said auxiliary pallet means, said first end of said auxiliary pallet including a pair of separable frame members which can be moved apart to allow said traction cord to pass between the separable frame members, whereby said auxiliary pallet means can be rigidly connected to said pivotal connecting means without interrupting traction applied to the patient.

* * * * *

UNITED STATES PATENT AND TRADEMARK OFFICE
CERTIFICATE OF CORRECTION

PATENT NO. : 4,244,358

DATED : January 13, 1981

INVENTOR(S) : Noel Pyers

It is certified that error appears in the above—identified patent and that said Letters Patent is hereby corrected as shown below:

On The Title Page Insert:

-- (73) Assignee: David P. Ulfers and George F. Elias, Jr.,

Tucson, Arizona, part interest. --.

Signed and Sealed this

Twenty-eighth Day of April 1981

[SEAL]

*Attest:*

RENE D. TEGTMEYER

*Attesting Officer* *Acting Commissioner of Patents and Trademarks*